United States Patent
Godin et al.

(10) Patent No.: US 7,890,291 B2
(45) Date of Patent: Feb. 15, 2011

(54) METHOD AND DEVICE FOR DETECTING A SUBSTANTIALLY INVARIANT ROTATION AXIS

(75) Inventors: Christelle Godin, Brignoud (FR); Stèphane Bonnet, Seyssinet (FR); Alain Barraud, Froges (FR); Suzanne Lesecq, Froges (FR)

(73) Assignees: Commissariat a l'Energie Atomique, Paris (FR); Universite Joseph Fourier, Grenoble (FR); Institut National Polytechnique de Grenoble, Grenoble (FR)

( * ) Notice: Subject to any disclaimer, the term of this patent is extended or adjusted under 35 U.S.C. 154(b) by 0 days.

(21) Appl. No.: 12/108,981

(22) Filed: Apr. 24, 2008

(65) Prior Publication Data

US 2008/0281555 A1    Nov. 13, 2008

(30) Foreign Application Priority Data

Apr. 25, 2007    (FR) .................................. 07 54693

(51) Int. Cl.
*G01C 17/00*    (2006.01)

(52) U.S. Cl. ..................................... 702/153
(58) Field of Classification Search ................ 702/153
See application file for complete search history.

(56) References Cited

U.S. PATENT DOCUMENTS

| | | | | |
|---|---|---|---|---|
| 3,731,521 A | * | 5/1973 | Solov et al. ................. | 73/1.77 |
| 4,884,771 A | * | 12/1989 | Scheit et al. ................. | 244/165 |
| 5,105,152 A | | 4/1992 | Pauly | |
| 6,820,025 B2 | | 11/2004 | Bachmann et al. | |
| 7,269,532 B2 | * | 9/2007 | David et al. ................. | 702/151 |

FOREIGN PATENT DOCUMENTS

FR    2 838 185    10/2003

OTHER PUBLICATIONS

Rui, et al., "Nonlinear Attitude and Shape Control of Spacecraft with Articulated Appendages and Reaction Wheels", IEEE Transactions on Automatic Control, vol. 45, No. 8, Aug. 2000.

Non-Final Office Action, Dated Sep. 15, 2009—for U.S. Appl. No. 12/158,631, filed Jun. 20, 2008—(7 pgs).

Benoit Le Callennec and Ronnan Boulic—"*Robust Kinematic Constraint Detection for Motion Data*"—Eurographics/ACM SIGGRAPH Symposium on Computer Animation (2006)—(10 pgs).

* cited by examiner

*Primary Examiner*—Aditya Bhat
(74) *Attorney, Agent, or Firm*—Brinks Hofer Gilson & Lione

(57) ABSTRACT

A method for detecting a substantially invariant rotation axis of a motion of a mobile body equipped with at least one inertial or magnetic sensor with three sensitive axes that includes acquiring physical measurements with respect to the three sensitive axes of the sensor, the physical measurements including at least three samples at different times, estimating a substantially invariant rotation axis in the physical measurements space, and identifying the estimated axis as the substantially invariant rotation axis of the motion. In one aspect, the method is applicable for estimating the motion of a mobile body rotating about a substantially invariant axis.

16 Claims, 4 Drawing Sheets

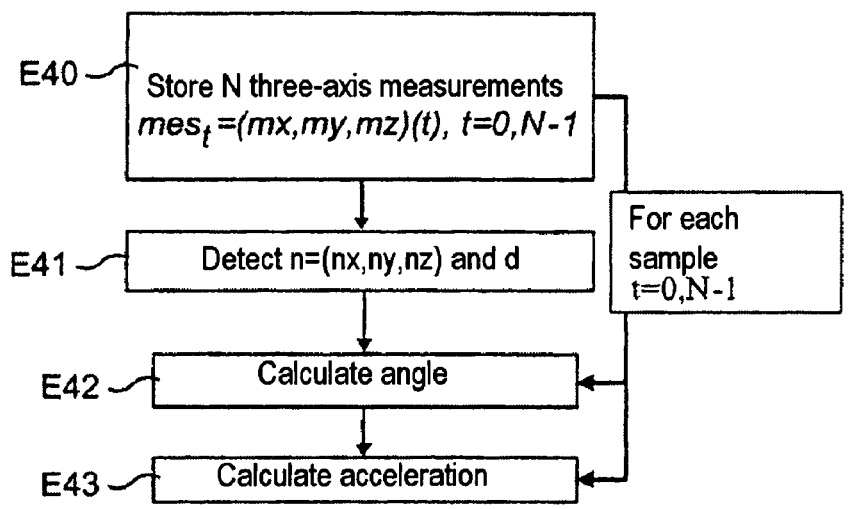
Fig. 4
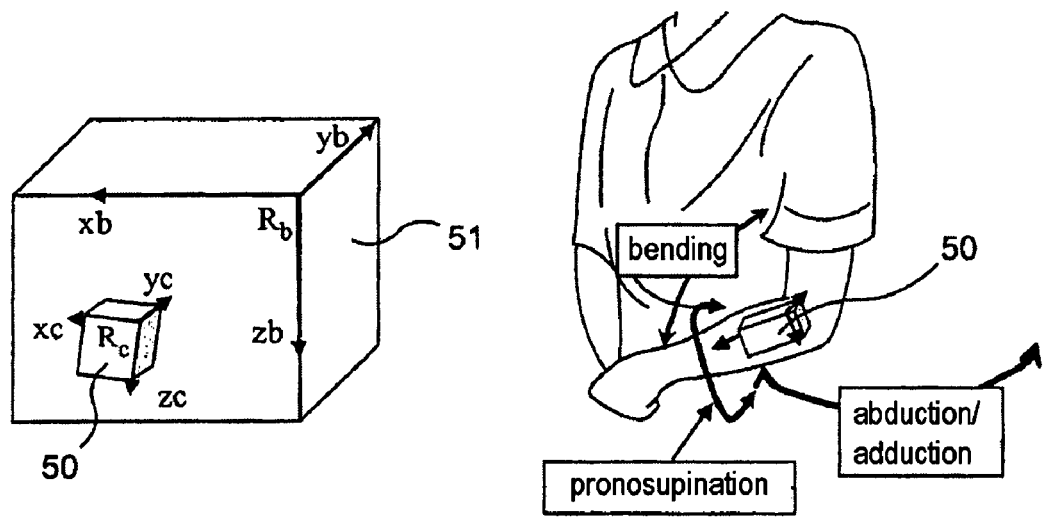
Fig. 5
Fig. 6

METHOD AND DEVICE FOR DETECTING A SUBSTANTIALLY INVARIANT ROTATION AXIS

CROSS-REFERENCE TO RELATED APPLICATION

This application claims priority to French Patent Application No. 0754693, filed Apr. 25, 2007, which is incorporated by reference herein.

TECHNICAL FIELD

The present invention concerns a method for detecting a substantially invariant rotation axis of the motion of a solid. It also concerns a method for estimating the motion of a solid and a method for calibrating an inertial or magnetic sensor with three sensitive axes. In a correlated way, the present invention concerns a device for detecting a substantially invariant rotation axis of the motion of a solid. Generally, the present invention concerns the field of motion capture. The fields of application are varied and cover in particular the biomedical field, for the observation of persons, and the sports field, for the analysis of the motion of a sportsperson or their equipment (racket, ball, etc.). It also applies to the field of automobiles or robotics, as well as to virtual reality, and generally to any application including a mobile body the motion whereof is to be determined or observed.

BACKGROUND

There are known in particular inertial systems consisting of one or more sensors selected in particular from accelerometers, magnetometers or rate gyros, having one or more sensitive axes.

These inertial systems have the advantage of being autonomous and of not requiring the environment in which the motion of a mobile object is observed to be fitted out with equipment beforehand.

There is known in particular a device for sensing rotation of a solid as described in the document FR 2 838 185.

The principle of observing a mobile body in motion is to seek magnitudes representing the displacement and orientation of the mobile body, or its speed and rotation speed, or its acceleration and angular acceleration.

In practice, the sensors are placed on the observed mobile body and the aim is to determine a motion that potentially has six degrees of freedom, i.e. three degrees of freedom corresponding to the orientation of the solid in space and three degrees of freedom corresponding to the position of the mobile body.

Solving systems of equations to determine magnitudes representing the motion of a solid is generally complex and necessitates solution systems in which certain constraints are known in advance.

SUMMARY

An aim of the present invention is to overcome the drawbacks of earlier motion estimating systems and to propose a method that is particularly suitable for processing the motion of a mobile body having a substantially invariant rotation axis.

A first aspect of the present invention is directed to a method for detecting a substantially invariant rotation axis of a motion of a mobile body equipped with at least one inertial or magnetic sensor with three sensitive axes.

According to the invention, this detection method comprises the following steps:
acquisition of physical measurements with respect to the three sensitive axes of the sensor, the physical measurements comprising at least three samples at different times; estimation of a substantially invariant rotation axis in the physical measurements space; and identification of said estimated axis as the substantially invariant rotation axis of the motion.

The applicant has found that by determining the substantially invariant rotation axis among the measurements obtained at the output of the same sensor it is possible to determine the substantially constant rotation axis of the motion of the mobile body equipped with that sensor.

Estimating the rotation axis in the physical measurements space requires at least three different measurements at different times and with respect to the three sensitive axes of the sensor, to enable determination of the coordinates of the estimated rotation axis.

In practice, the detection method further comprises the following steps: calculation of an indicator of the variations of the rotation axis;
comparison of the value of the indicator with a predetermined threshold value; and
validation of the estimated rotation axis as the substantial invariant rotation axis of the motion if the value of the indicator is less than the predetermined threshold value which is advantageously equal to the value of the noise affecting the physical measurements from said sensor.

Accordingly, thanks to an indicator of variations of the estimated rotation axis, it is possible to obtain an indication of the variations of the rotation axis of the motion. If the value of this indicator is sufficiently low, i.e. of the same order as the noise affecting the physical measurements from the observed sensor, the motion can be considered to correspond faithfully to rotation about a substantially invariant axis. Thus it is possible to validate the estimated rotation axis in the physical measurements space as the substantially invariant rotation axis of the motion of the mobile body.

According to one practical embodiment of the invention, when the mobile body is equipped at least with a magnetometer having three sensitive axes and an accelerometer having three sensitive axes, the detection method comprises the following steps:
acquisition of the physical measurements with respect to the three sensitive axes of the magnetometer and the accelerometer, respectively, the physical measurements comprising at least three samples at different times;
estimation of the substantially invariant rotation axes in the said physical measurements spaces of said magnetometer and said accelerometer, respectively; and
validation as the substantially invariant rotation axis of said motion of a linear combination of the estimated rotation axes for said physical measurements from the magnetometer and from the accelerometer, the coefficients of the combination being not strictly between 0 and 1, their sum being equal to 1, and being a function of the values of the indicators of the variations of the rotation axes of the magnetometer and/or the accelerometer.

In particular, if one of the coefficients of the combination is equal to zero, it is possible to use either sensor (magnetometer or accelerometer) providing the most reliable estimate of the substantially invariant rotation axis.

In particular, if the rotation occurs about an axis of the physical field considered (the gravitational field in the case of accelerometers, the terrestrial magnetic field in the case of magnetometers), it is possible to determine the invariant rotation axis using the other sensor if the indicator of the variations of the rotation axis estimated by means of the physical measurements from the sensor associated with the invariant physical field will necessarily be inadequate, i.e. very much greater than the noise affecting the physical measurements obtained by that sensor.

In one practical embodiment of the invention, the detection method further includes a step of transformation of the coordinates of the estimated rotation axis in the measurement frame of reference of the sensor into coordinates in a geophysical frame of reference, such as an NED (North-East-Down) frame of reference.

A second aspect of the present invention concerns a method for estimating a motion of a mobile body equipped with at least one inertial or magnetic sensor with three sensitive axes, the motion comprising rotation about a substantially invariant axis.

According to the invention the estimation method comprises the following steps:

detection of a substantially invariant rotation axis by the detection method according to the invention;

determination of the rotation angle of the mobile body about the substantially invariant rotation axis.

If the sensor is a magnetometer or a goniometer and the mobile body is further equipped with an accelerometer, the estimation method further comprises a step of determining the acceleration of the mobile body.

Thanks to the method for the invention of detecting a substantially invariant rotation axis, the method for estimating the motion of a mobile body is facilitated if the number of unknowns to be determined is limited to the determination of the rotation angle, and where appropriate the acceleration of the mobile body.

Following detection in accordance with the invention of the invariant rotation axis, it is possible to calculate this motion in two steps, firstly seeking the rotation angle, and then calculating the acceleration of the mobile body.

A third aspect of the invention concerns a method for calibrating an inertial or magnetic sensor with three sensitive axes for determining a rotation matrix suitable for transforming coordinates expressed in a measurement frame of reference of the sensor into coordinates expressed in a predetermined frame of reference stationary with respect to a mobile body carrying the sensor.

This calculation method comprises the following steps:

acquisition of at least two series of physical measurements by the sensor respectively corresponding to the rotation of the mobile body with respect to at least two of the three axes of the predetermined frame of reference stationary with respect to the mobile body;

determination from each of the two series of coordinates of each of the rotation axes corresponding to one of said two of the three axes of the predetermined frame of reference stationary with respect to the mobile body in the frame of reference of the physical measurements from the sensor according to the detection method according to the invention; and generation of a rotation matrix from the determined coordinates of said at least two of the three rotation axes.

This calibration method means that the measures obtained by the sensor can then be expressed in a predetermined frame of reference linked to the observed mobile body, such as a casing enclosing the sensor or an anatomical feature of a person on whom the sensor is placed.

Finally, a fourth aspect of the present invention concerns a device for detecting a substantially invariant rotation axis of a motion of a mobile body equipped with at least one inertial or magnetic sensor with three sensitive axes.

This detector device comprises means adapted to implement the detection method according to the invention.

This detection device has features and advantages analogous to those described hereinabove in relation to the detection method.

Other features and advantages of the invention will become apparent in the course of the following description.

BRIEF DESCRIPTION OF THE DRAWING

In the appended drawings, provided by way of nonlimiting example:

FIG. 4 shows an algorithm illustrating one embodiment of a method for the invention for estimating a motion of a mobile body;

FIG. 5 is a diagram showing one embodiment of a calibration device of the invention integrated into a casing;

FIG. 6 is a diagram showing one embodiment of a calibration device of the invention in which the sensor is positioned on an anatomical feature.

DETAILED DESCRIPTION

Figure 1:
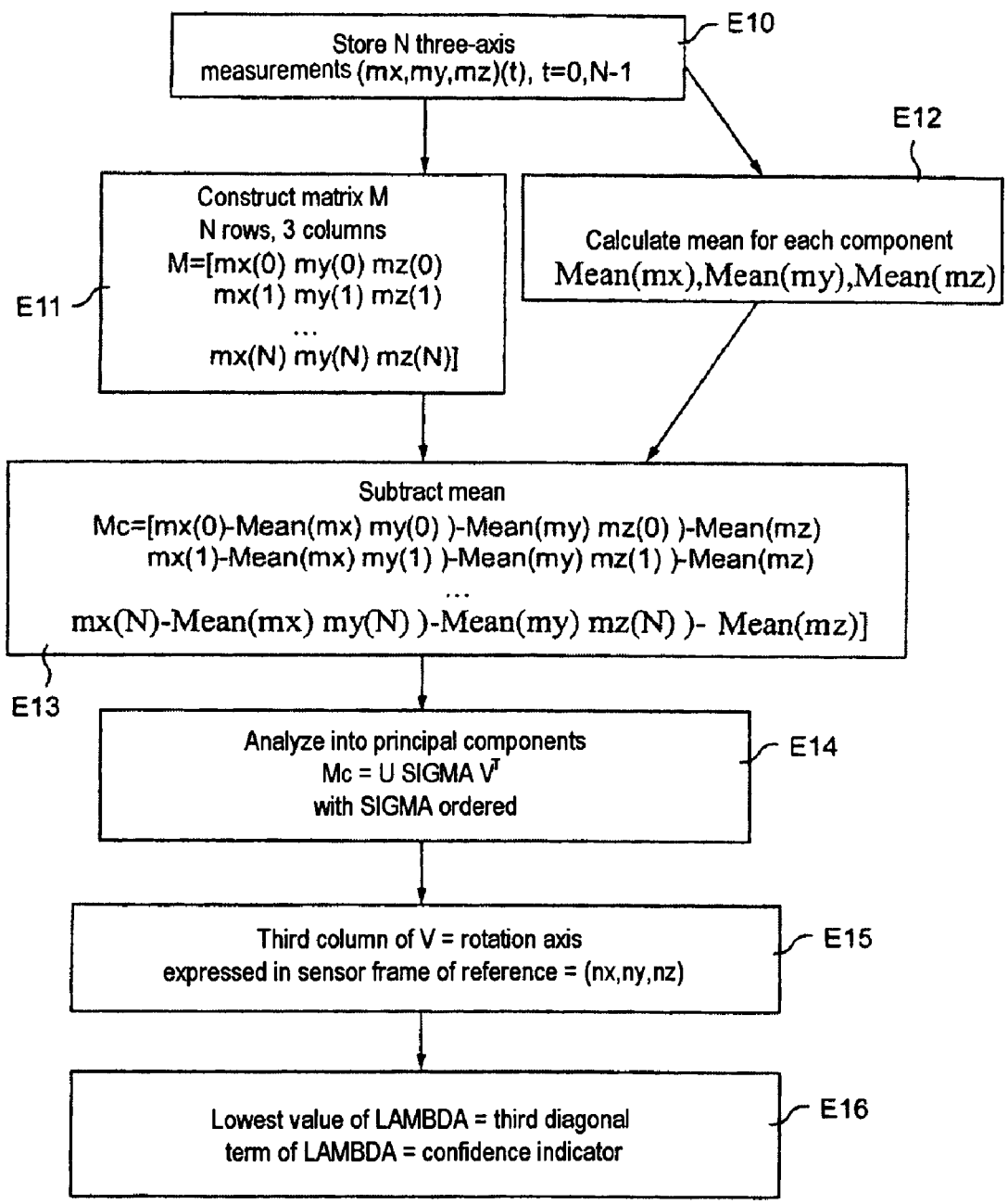
FIG. 1 shows an algorithm illustrating a first embodiment of a method for the invention for detecting a substantially invariant rotation axis.

A first embodiment of a method for detecting a substantially invariant rotation axis of a motion of a mobile body equipped with a sensor with three sensitive axes is described first with reference to FIG. 1.

This method can be applied to studying the motion of a mobile body in numerous applications where the motion of the mobile body corresponds to rotation about a fixed or substantially invariant axis.

There are many applications in which the motion of the observed mobile body corresponds to a rotation about an axis, generally also with no motion along this rotation axis, and so the motion is performed in a plane and can be considered a planar motion.

For example, such motion is observed in the case of a vehicle with zero roll and pitch. The rotation of the vehicle corresponds to a rotation about a fixed vertical axis, corresponding to a yaw motion. The vertical acceleration is generally zero and so the motion of the vehicle is a planar motion.

Similarly, motion of the members of a person (arms, legs, and the like) is observed in a plane if there is only one rotation axis of one joint and one angle that varies over time.

The motion of a wheel rolling without slipping on a plane and in a straight line also corresponds to motion about a rotation axis, perpendicular to the plane of the wheel.

The movement of a computer mouse in a plane about an axis orthogonal to that plane is also a planar motion that can be observed in the context of the present invention.

Generally speaking, the method for detecting the substantially invariant rotation axis of such motion is implemented by means of a detector device equipped with at least one sensor having three sensitive axes, for example an accelerometer, a magnetometer or a three-axis rate gyro.

In theory, the detection method consists in estimating a substantially invariant rotation axis in the space of the physical measurements obtained by the sensor with three sensitive axes.

In the embodiment illustrated in FIG. 1, it is considered that the substantially invariant rotation axis in the measurements space corresponds to the axis showing the least variation of the measurements for the magnetometer and the accelerometer and that showing the greatest variation for the rate gyro.

Each measurement at a time t obtained at the output of a sensor with three sensitive axes is considered as a point in the three-dimensional measurements space.

Thus the invariant axis is the axis with respect to which magnetometer or accelerometer measurements show the least variation on that axis, and in particular, for which the standard deviation of points projected onto that axis is the lowest.

In the case of a rate gyro, this will be the axis with the greatest variation, since the rate gyro measures the value of the rotation about each of its axes.

Figure 2:
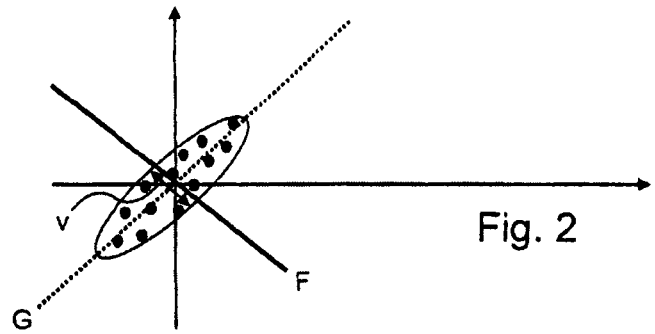
FIG. 2 is a diagram illustrating the step of estimating a substantially invariant rotation axis in accordance with the invention.

FIG. 2 is a simplified illustration in a two-dimensional space of measurements represented by a set of points.

Of course, this diagrammatic representation can be extended to a space with three dimensions.

The axis F showing the least variation and the axis G showing the greatest variation are shown in FIG. 2.

The arrow v in the direction of the axis F showing the least variation corresponds to the standard deviation of the measurements projected onto that axis and thus corresponds to an indicator of variations of the rotation axis. The lower this variance v, the more closely the observed motion corresponds to rotation about a fixed axis.

There will be described with reference to FIG. 1 a method for detecting a substantially invariant rotation axis enabling the axis showing the least variation to be determined from a principal component analysis.

In practice, a step E10 of acquiring physical measurements with respect to the three sensitive axes of the sensor is executed.

The physical measurements comprise N samples at different times with respect to the three sensitive axes of the sensor.

To enable the problem to be solved, N is greater than or equal to 3.

Thus N measurements (mx, my, mz)(t) are stored with t varying from 0 to N−1.

A step E11 of constructing a matrix M is then executed so that each row corresponds to a temporal sample of the measurements and each column corresponds to a component obtained with respect to the sensitive axes X, Y, Z of the sensor.

Thus:

$$M = [mx(0) \quad my(0) \quad mz(0)$$
$$mx(1) \quad my(1) \quad mz(1)$$
$$...$$
$$mx(N) \quad my(N) \quad mz(N)]$$

At the same time, a step E12 of calculating the mean value obtained for each component with respect to the sensitive axes X, Y, Z is executed.

Thus in practice a mean value of the measurements obtained is calculated for each column of the matrix M.

The following mean values are determined:
Mean(mx), Mean(my), Mean(mz)

A homogenization step E13 is then executed to subtract the mean value calculated in the step E12 from each element of the matrix M to obtain a matrix Mc:

$$Mc = [mx(0)\text{-Mean}(mx) \quad my(0)\text{-Mean}(my) \quad mz(0)\text{-Mean}(mz)$$
$$mx(1)\text{-Mean}(mx) \quad my(1)\text{-Mean}(my) \quad mz(1)\text{-Mean}(mz)$$
$$...$$
$$mx(N)\text{-Mean}(mx) \quad my(N)\text{-Mean}(my) \quad mz(N)\text{-Mean}(mz)]$$

It is possible to effect an analysis into principal components of the matrix Mc obtained in an analysis step E14.

Determining the axis showing the least variation by a principal component analysis is known in the art and need not be described in detail here. See in particular the description of this technique in Jolliffe I. T., Principal component analysis, 2nd edition, Springer 2002 or Jackson J. E., A User's Guide to Principal Components, John Wiley and Sons, 1991, p. 4-25.

In theory, this principal components analysis amounts to seeking a 3×3 unitary matrix V in which each column vector is of unitary norm and orthogonal to the other column vectors, a 3×3 diagonal ordered matrix SIGMA with positive elements of the diagonal in decreasing order, and an N×N unitary matrix U such that:

$$Mc = U \text{ SIGMA } V^T$$

These matrices can be obtained by decomposing into singular values the matrix Mc or decomposing into eigenvalues and eigenvectors the matrix $S=(N-1) Mc^T Mc$, so that $SV=V$ LAMBDA, where LAMBDA is a diagonal matrix that contains the eigenvalues of S. Moreover, LAMBDA (i, i)=$(N-1)^{-1}$ SIGMA $(i, i)^2$.

The columns of the unitary matrix V are called factorial axes and the rotation axis looked for is expressed in the frame of reference associated with the captors, corresponding to the projection axis on which the measurements have the lowest variance, corresponds to the third column of the unitary matrix V.

The value LAMBDA (3, 3) in the third column of the diagonal matrix LAMBDA corresponds to the variance associated with the axis determined in this way.

Thus it is possible to estimate the substantially invariant rotation axis in an estimation step E15 from the factorial axis of the third column of the unitary matrix V, the rotation axis therefore being expressed in the frame of reference associated with the sensors. Hereinafter, this rotation axis is denoted by its coordinates in the frame of reference of the sensor, as follows:

(nx,ny,nz)

To validate the rotation axis estimated in this way, the detection method further includes a step E16 of calculating a rotation axis variation indicator.

Thus the value d is calculated such that:

$$d = \frac{\text{LAMBDA}(3, 3)}{\text{LAMBDA}(1, 1) + \text{LAMBDA}(2, 2) + \text{LAMBDA}(3, 3)}$$

This value d of the indicator is an indication as to the validation of the estimated rotation axis as the invariant rotation axis of the motion.

The smaller the value d, the more valid the hypothesis whereby the motion of the mobile occurs around a constant or substantially invariant rotation axis.

In practice, the value of LAMBDA (3, 3) of the indicator is compared with the value of the noise affecting the physical measurements obtained by the sensor. If the value of LAMBDA (3, 3) of the indicator is substantially equal to or of the same order of magnitude as the noise value, the estimated rotation axis (nx, ny, nz) is validated as the substantially invariant rotation axis of the motion of the mobile body.

Also, the variations with respect to the other axes must be high: LAMBDA (3, 3)+LAMBDA (2, 2)+LAMBDA (1, 1) must be large, which guarantees that the motion is of sufficiently large amplitude.

In practice, if d is close to ⅓, the three axes have equivalent variations, and nothing can be concluded. The "constant rotation axis" hypothesis is retained only if d<threshold, which threshold is taken as equal to 0.1, for example.

Another indicator can be d*=LAMBDA (3, 3)/LAMBDA (2, 2), which should be small compared to 1. The "constant rotation axis" hypothesis is retained only if d*<threshold, which threshold is taken as equal to 0.1, for example.

Other methods can be used for estimating the lowest variation axis in the measurements obtained by an inertial or magnetic sensor.

The least squares method can also be used, for example.

In theory, the least squares method amounts to estimating the axis n on which the projection of the measurements M is constant. That axis n can be calculated from the following formula:

$$n = pinv(M)O$$

where pinv(M) is the generalized inverse of the matrix M as constructed in the step E11 described with reference to FIG. 1, n is a column vector with three components $n = (nx, ny, nz)^T$, and O is a vector of N rows and 1 column, all elements of which are equal to 1.

The vector n is normalized to obtain the director vector of the normal to the plane.

Note that the rotation axis detection method described above can generally be executed for different types of inertial or magnetic sensors, for example an accelerometer with three sensitive axes, a magnetometer with three sensitive axes or a rate gyro with three sensitive axes.

However, in the case of a rate gyro type inertial sensor, the estimated rotation axis correspond not to the axis showing the least variation of the measurements but on the contrary to the axis showing the greatest variation. The rotation axis variation indicator used then corresponds to the variance or the standard deviation calculated for the two axes orthogonal to the estimated rotation axis.

Of course, a single inertial or magnetic sensor can detect the constant rotation axis in the physical measurements at the output of this sensor if the value of the rotation axis variation indicator is substantially equal to the value of the noise affecting the associated physical measurements.

In particular, when the sensor is an accelerometer, if the standard deviation of the measurements projected onto the estimated rotation axis is substantially equal to the noise affecting the sensor, the estimated rotation axis is validated as the substantially invariant rotation axis of the motion and additionally the motion is considered planar.

In practice, if the mobile body is equipped with a plurality of sensors and, for example, at least a magnetometer with three sensitive axes and an accelerometer with three sensitive axes, it is possible to estimate the rotation axis by the method described above in the physical measurements space associated with each of the sensors, i.e. with the magnetometer and with the accelerometer.

There is then validated as the substantially invariant rotation axis of the motion a linear combination of the estimated rotation axes for the physical measurements of the magnetometer and the accelerometer.

The coefficients of the linear combination are not strictly between 0 and 1 and their sum is equal to 1.

These coefficients are a function of the values of the rotation axis variation indicators of the magnetometer and/or the accelerometer.

If one of the coefficients of the combination is equal to 0, this amounts to using the sensor (either the magnetometer or the accelerometer) producing the most reliable estimate of the substantially invariant rotation axis.

It is therefore possible to circumvent the situation in which the rotation is about the axis of the physical field concerned and associated with the sensor, i.e. the gravitational field in the case of accelerometers and the terrestrial magnetic field in the case of magnetometers.

In this case, the estimate of the rotation axis will be highly inadequate for the sensor concerned and the detection method will automatically validate the estimated rotation axis for the other sensor as the substantially invariant rotation axis of the motion.

For example, in the case of motion about a vertical axis (or in a horizontal plane), like that of a mouse on a desk, using an accelerometer as the inertial sensor in the detection method would not be satisfactory. On the other hand, the vertical rotation axis of the motion could be estimated using a magnetometer.

Figure 3:
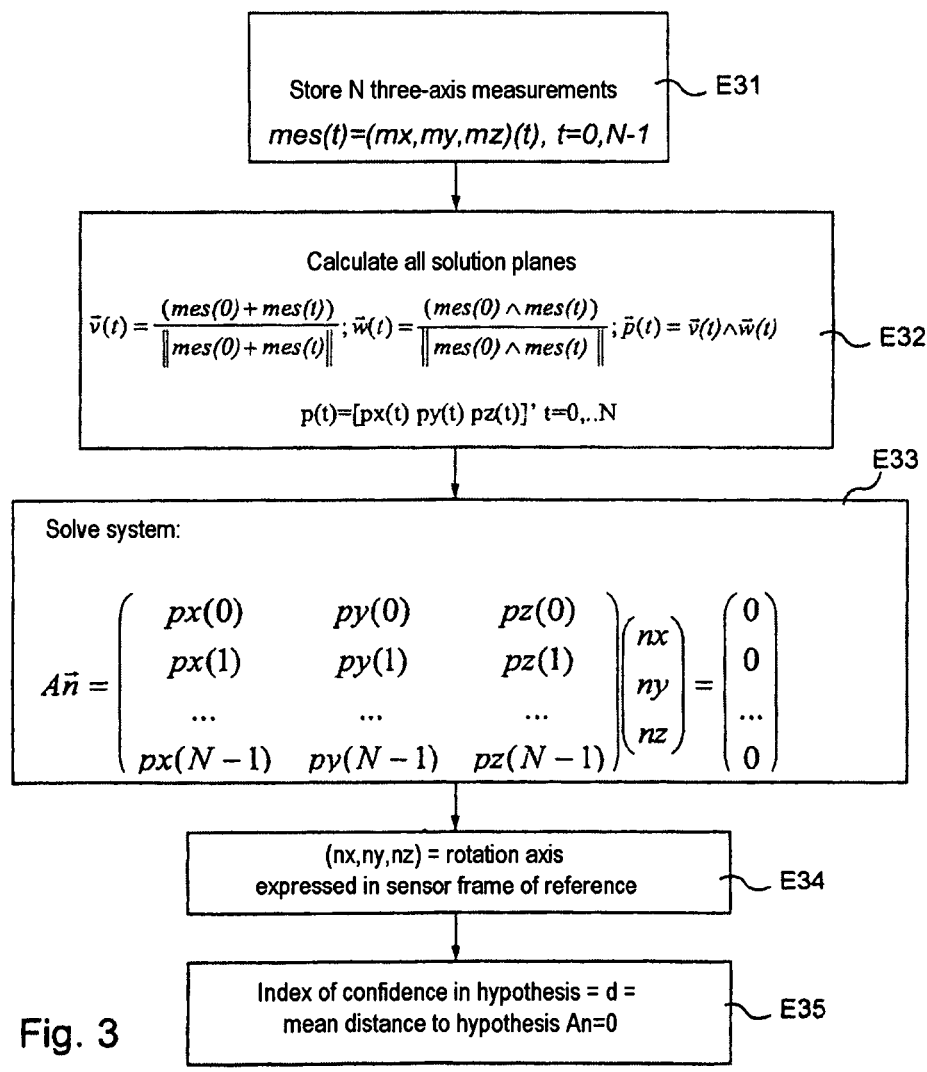
FIG. 3 shows an algorithm illustrating a second embodiment of a method for the invention for detecting a substantially invariant rotation axis.

A second embodiment of the invention is described with reference to FIG. 3 in which the rotation axis detection method begins with a step of vectorial calculation applied to the physical measurements obtained for the three sensitive axes of the sensor.

In theory, each measurement is considered as a vector in a three-dimensional space.

The constant rotation axis in the measurements space is determined by obtaining the intersection of a number of planes each corresponding to all possible rotation axes for moving from one vector to another. In practice, the vectors are grouped and analyzed two by two in order to determine each plane.

The distance between the planes at the intersection is an indicator of the variations of the rotation axis.

As in the previous embodiment, by calculating this indicator and comparing the value of this indicator with the noise value of the physical measurements from the sensor, it is possible to validate the estimated rotation axis, and in particular, the axis corresponding to the intersection of the planes, as the substantially invariant rotation axis of the motion if the value of the indicator is substantially equal to the noise value of the physical measurements from the sensor.

In practice, a storage step E31 acquires physical measurements for the three sensitive axes of the sensor.

Thus N measurements are obtained for the three sensitive axes:

$$mes(t) = (mx, my, mz)(t), t=0, \ldots, N-1$$

A step E32 of calculating all the solution planes P(t) is then executed in the following manner.

The following three vectors are defined for each time t:

$$\vec{v}(t) = \frac{(mes(0) + mes(t))}{\|mes(0) + mes(t)\|};$$

$$\vec{w}(t) = \frac{(mes(0) \wedge mes(t))}{\|mes(0) \wedge mes(t)\|};$$

$$\vec{p}(t) = \vec{v}(t) \wedge \vec{w}(t)$$

$$= \begin{vmatrix} px(t) \\ py(t) \\ pz(t) \end{vmatrix}$$

In practice, at each time t, the axis of the rotation that the mobile body has effected between the time t=0 and the time t necessarily belongs to the plane defined by the vectors $\vec{v}(t)$ and $\vec{w}(t)$, which again corresponds to the equation of a plane $\vec{p}(t) \cdot \vec{n} = 0$.

Thus if there is a constant rotation axis in the motion of the observed mobile body, it corresponds to the intersection of all the planes defined by the vectors $\vec{v}(t)$ and $\vec{w}(t)$, with t varying from 0 to N−1.

On the other hand, if the intersection exists, the hypothesis that the motion is performed about a constant rotation axis can be considered to be validated and that rotation axis can be considered to correspond to the intersection of the planes.

In practice, a step E33 of solving the system is executed starting with the construction of a matrix A the rows whereof correspond to the N samples and the columns whereof correspond to the three components of the vector $\vec{p}$:

$$A = \begin{pmatrix} px(0) & py(0) & pz(0) \\ \ldots & & \ldots \\ px(N-1) & py(N-1) & pz(N-1) \end{pmatrix}$$

Seeking the rotation axis $\vec{n}(nx, ny, nz)$ amounts to solving the equation $A\vec{n}=0$, that is to say:

$$A\vec{n} = \begin{pmatrix} px(0) & py(0) & pz(0) \\ px(1) & py(1) & pz(1) \\ \ldots & \ldots & \ldots \\ pz(N-1) & py(N-1) & pz(N-1) \end{pmatrix} \begin{pmatrix} nx \\ ny \\ nz \end{pmatrix} = \begin{pmatrix} 0 \\ 0 \\ \ldots \\ 0 \end{pmatrix}$$

The coordinates of the vector $\vec{n}$ can be obtained by decomposing the matrix A into singular values as described hereinabove so that $A=USV^T$.

In the same way as for the principal component analysis, the diagonal terms are classified in decreasing order.

The rotation axis $\vec{n}$ then corresponds to the third column of the unitary matrix V.

The values of the diagonal of the matrix S are used as previously to calculate the value d of an indicator of the variations of the rotation axis, which corresponds to the mean distance with the hypothesis $A\vec{n}=0$.

It will be noted that solving the system can be facilitated if the number N of samples is high, by first effecting orthogonal triangularization of the matrix A and thereafter applying decomposition into singular values directly to the triangularized matrix.

Moreover, the estimate of the vector n can be improved, in particular by eliminating from the matrix the measurements for which mes(t) and mes(0) are close.

If the distance between the vectors is small, the orientation of the vector w is strongly disturbed by the noise affecting the measurements, and so the general estimate of the vector $\vec{n}$ by the matrix A is also disturbed.

To limit this effect, it is possible to eliminate from the matrix A the rows corresponding to observations such that the distance between the vectors mes(t) and mes(0) is less than a threshold value s that is predetermined as a function of the noise affecting the measurements obtained at the output of the associated sensor.

Note that the determination method using vectorial analysis can be applied to measurements obtained from magnetometers in the absence of magnetic disturbances or measurements obtained at the output of accelerometers in the absence of acceleration.

On the other hand, this type of vectorial calculation on the physical measurements is not applicable to a rate gyro type inertial vector.

In the embodiments described hereinabove, it is necessary to have a number N of samples at least equal to 3 in order to detect the rotation axis.

Moreover, the distance between the measurements must be greater than the noise affecting the measurements.

Thus for a magnetometer for which the noise is substantially equal to 0.1, it is necessary to have a distance between the measurements of at least 0.3.

In practice, this means that the detection method for determining the rotation axis is particularly suitable if the N samples cover sufficiently large rotation displacements about that rotation axis.

The detection method described hereinafter can be complemented by a step of transformation of the coordinates of the estimated rotation axis n=(nx, ny, nz) in the measurement frame of reference of the sensor into coordinates in a geophysical frame of reference.

The geophysical frame of reference can typically be the North-East-Down (NED) frame of reference.

For example, the coordinates of the rotation axis in the NED geophysical frame of reference can be calculated from measurements projected onto the rotation axis expressed in the frame of reference of the sensor in the following manner.

In the geophysical frame of reference NED, the gravitational field is written g=(0, 0, 1) and the magnetic field b=(bx, 0, bz).

The magnetic field varies as a function of the measurement location, the values bx and bz being the reference of the terrestrial magnetic field at the location where the measurement is effected.

For example, in France, $bx \simeq 1/2$ and $$bz \simeq \frac{\sqrt{3}}{2}.$$

It is therefore the coordinates $nz_{NED}$, $nx_{NED}$, $ny_{NED}$ of the vector in the geophysical frame of reference NED that are required.

If the accelerometer measurements are expressed in the new frame of reference by effecting the matrix product newmesacc=$mes_a$V, the third component should be seen to be quasi-constant. It reflects the inclination of the plane in the inertial frame of reference and corresponds to the coordinate $nz_{NED}$.

$nz_{NED}$=mean(new*mesaccz*)

Similarly, if the accelerometer measurements are expressed in the new frame of reference by effecting the matrix product newmesmag=Mes$_b$V, the third component should be seen to be quasi-constant. It is the conjoint reflection of the inclination of the plane and its orientation relative to local magnetic north in the inertial frame of reference, and corresponds to the coordinate z.

We have tmp=mean (newmesmagz)

$$tmp=0.5nx_{NED}+0.86nz_{NED}$$

or $nx_{NED}=2*tmp-sqrt(3)*nz_{NED}$

Finally, the coordinate $ny_{NED}$ can be determined by seeking the normed vector with the coordinates determined previously:

$$ny_{NED}=\pm\sqrt{1-nx_{NED}^2-nz_{NED}^2}$$

Starting from detecting a substantially invariant rotation axis by the method described above, it is possible to estimate the complete motion of a mobile body equipped with at least one inertial or magnetic sensor with three sensitive axes.

The method for estimating the motion of a mobile is illustrated by FIG. 4 in particular.

After a step E40 of storing N measurements, corresponding to the storage steps E10 or E31 in FIGS. 1 and 3, a detection step E41 is executed as described hereinabove in order to detect a rotation axis represented by its coordinates n=(nx, ny, nz).

It is then possible to calculate successively the rotation angle in a calculation step E42 and then the acceleration of the mobile body in a calculation step E43, for each measurement sample at times t between 0 and N−1 and for the subsequent samples if the rotation axis no longer varies.

In practice, the step E42 of calculating the rotation angle can be implemented in the following manner.

Once the rotation axis has been estimated, the angle θ of the rotation effected can be calculated at any time by an analytical calculation:

$$\theta = +2\arcsin\frac{\|mes(0)-mes(t)\|}{\sqrt{\|mes(0)-mes(t)\|^2+\|mes(0)+mes(t)\|^2(\vec{w},\vec{n})^2}}$$

The symbol θ corresponds to that for reconstructing the measurement mes(t) as well as possible.

A second method estimating θ by optimization could be used:

$$\min_\theta(\|mes(t)-M(\tilde{n},\theta)mes(0)\|^2)$$

where $M(\tilde{n},\theta)$ is the rotation matrix of axis n and angle θ.

The matrix V obtained by principal component analysis as described with reference to step E14 in FIG. 1 can also be used to change the data frame of reference.

Using the same notation as before, measurements in the new frame of reference are given by M'=VM. The third component will be constant in this frame of reference.

For each time (row of matrix M' of N rows by 3 columns), the angle of the rotation is the angle formed by the two 2D vectors (their coordinates correspond to the first two columns).

In practice, what is required is the angle between two vectors corresponding to two rows of the matrix that correspond to the rotation effected between those two times.

To this end, these vectors can be expressed in polar coordinates (length, orientation), for example, and then the difference of their orientations obtained. Their scalar product can also be used.

In the case of an accelerated movement, once the orientation of the mobile object has been estimated at each time t using a magnetometer or a goniometer, the acceleration of the mobile body can be estimated using an accelerometer.

Knowing that the accelerometer measurements are written as follows:

$$mes(t)=M(n,\theta)(g-1)=M(n,\theta)(mes(0)-a)$$

where $M(n,\theta)$ is the rotation matrix for going from the fixed frame of reference to the mobile frame of reference, θ is the rotation angle, a is the required acceleration, and g is the gravitational field equal to mes(0) in the reference frame of reference at time 0.

The acceleration a of the mobile object can be estimated in the fixed frame of reference by:

$$\vec{a}=-M(\tilde{n},\theta)^T mes(t)+mes(0)$$

where a and mes(0) are expressed in the same fixed frame of reference.

In the particular case of planar motion, the acceleration a must be contained in the plane orthogonal to n. The problem to be solved then becomes an optimization with constraints:

$$\min_{\vec{a}}(\|mes(t)-M(\tilde{n},\theta)(mes(0)-\vec{a})\|^2)$$

where $\vec{n}\cdot\vec{a}=0$

This is a standard least squares problem with linear constraints that can again be solved by orthogonal factorization techniques.

Let H be the rotation matrix such that the axis x becomes the axis n (which is written Hn=[100]'). To find H, the triangular orthogonal decomposition of n can be effected. Let $\tilde{H}=H(:2:3)$ be the matrix consisting of the last two columns of H.

The acceleration of the mobile object is then obtained from:

$$\vec{a}_t=\tilde{H}\tilde{H}^T(-M(\tilde{n},\theta)mes(t)+mes(0))$$

By way of nonlimiting example, the observed motion can be walking. The sensor is placed on the tibial platform, for example. Precise alignment of the sensor is no longer necessary if only the angle described in the sagittal plane of walking is of interest.

The motion estimation method described hereinabove can be applied to each time segment corresponding to a stride or a step.

Moreover, thanks to the method for detecting an invariant axis described hereinabove, it is possible, by using this method, to calibrate a system of sensors, i.e. to determine a rotation matrix adapted to transform a measurement frame of reference of the sensor into a predetermined frame of reference stationary with respect to a mobile object carrying the sensor.

As shown in FIG. 5, if the sensor 50 is integrated into a casing 51, the axes xb, yb, zb of the predetermined frame of reference Rb are defined by edges of the casing 51.

The calibration method to be described hereinafter determines the rotation matrix for moving from the frame of reference Rc associated with the sensor 50 to the predetermined frame of reference Rb stationary with respect to the casing.

Similarly, as shown in FIG. 6, the sensor 50 can be placed on an anatomical feature, for example the forearm of a person.

The predetermined frame of reference then corresponds to an anatomical frame of reference defined by three anatomical rotation axes of that anatomical feature.

As shown clearly in FIG. 6, the axes of the anatomical frame of reference can be defined by the respective rotation axes of a bending movement of the forearm, a pronosupination movement of the forearm, and an abduction/adduction movement of the forearm.

In theory, the calibration method effects successive rotations about the three axes of the predetermined frame of reference Rb.

By then seeking for each of the three motions the coordinates of the corresponding rotation axis in the frame of reference of the sensor Rc it is possible to generate a rotation matrix in which the coordinates of each of the rotation vectors found correspond to a column of the rotation matrix for moving from the frame of reference of the sensor Rc to the predetermined frame of reference Rb stationary with respect to the mobile body.

Figure 7:
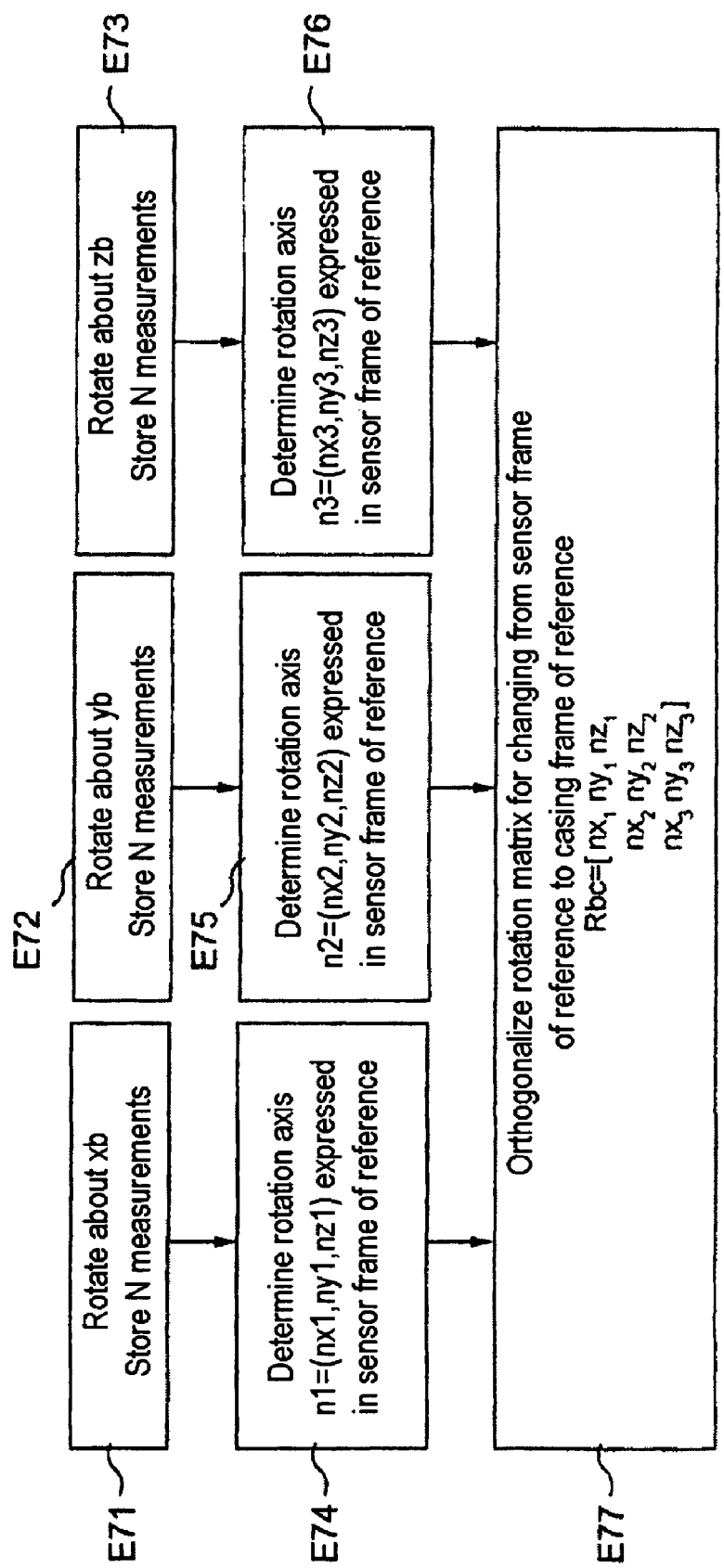
FIG. 7 shows an algorithm illustrating one embodiment of the method for the invention for calibrating a sensor.

As shown in FIG. 7, the calibration method includes in particular steps E71, E72, E73 for acquisition of physical measurements by the sensor, respectively corresponding to each rotation about the axes xb, yb, zb of the frame of reference Rb.

For each rotation motion, N measurement samples are stored as described hereinabove with reference to the storage step E10 shown in FIG. 1, for example.

From each stored set of N measurements a determination step E74, E75, E76 is executed in order to determine the coordinates of the three rotation axes n1, n2, n3 corresponding to the axes of the predetermined frame of reference Rb in the frame of reference Rc of the physical measurements from the sensor. These steps of determining the rotation axis E74, E75, E76 are executed as described hereinabove by the method for detecting a substantially invariant rotation axis.

A step E77 of generating a matrix Rbc is then executed using the coordinates of the rotation axes determined in the physical measurement frame of reference Rc:

Rbc=[nx1 ny1 nz1 nx2 ny2 nz2 nx3 ny3 nz3]

During the step E77 of generating the matrix Rbc, it is also possible to orthogonalize the matrix formed in this way by the three vectors n1, n2, n3 to render it unitary. The matrix Rbc then corresponds to a rotation matrix enabling measurements in the sensor frame of reference Rc to be expressed in the predetermined frame of reference Rb stationary with respect to the mobile body.

Accordingly, the measurements in the new frame of reference Rb can be expressed in the following manner:

$mes_b = Rbc\, mes_c$ in which $mes_b$ corresponds to measurements in the frame of reference associated with the casing and $mes_c$ corresponds to measurements in the frame of reference associated with the sensor.

It will be noted that in the method described hereinabove only two of the three rotations about axes of the predetermined frame of reference Rb can be effected, the coordinates of the third rotation axis then being obtained by orthogonalizing the matrix formed by the coordinates of the first two rotation axes determined by the detection method for the invention.

Also, the initial frame of reference may not be orthogonal (the axes are not mutually orthogonal). If the final frame of reference is orthogonal, then the matrix Rbc that effects the change of frame of reference then changes from data expressed in a non-orthogonal frame of reference to data expressed in an orthogonal frame of reference. For this it is essential to effect the three rotations and not to orthogonalize the matrix Rbc obtained.

The choice can also be made to pass through an intermediate orthogonal frame of reference and then to effect a change between two orthogonal frames of reference (in which case only two of the three rotations are necessary).

Accordingly, thanks to the method for the invention of detecting a substantially constant rotation axis, it is possible to reduce the number of degrees of freedom in the motion of an observed mobile object and thus to facilitate solving the systems for determining the parameters of that motion.

This method uses an inertia center comprising fewer inertial or magnetic sensors than prior art methods and in particular no rate gyro.

The method for estimating a motion using the detection of a constant rotation axis is particularly suitable for the situation in which the rotation axis varies slowly provided that the N measurement samples are stored over a small time window. It is thus possible, over each time window, to determine a substantially invariant rotation axis that is substantially invariant over that time window provided that there exist measurements that are sufficiently far apart over that time window, i.e. having a sufficient distance with respect to the noise affecting the measurements from the sensor.

Thus for each small time window the greatest distance between the measurement vectors taken two by two is calculated.

If that distance is less than a predetermined threshold that depends on the noise affecting the sensors, then the time window is enlarged and a sample of N measurements is stored over this new window.

If not, if the maximum distance between the measurement vectors is greater than the noise affecting the sensors, the rotation axis is calculated as indicated hereinabove with reference to the method for detecting a substantially invariant rotation axis and the indicator of variations of that rotation axis in order to validate the existence of a constant rotation axis in the observed motion.

Where appropriate, the angle and the acceleration of the motion over this time window can also be estimated if the motion of a mobile body in time is to be observed.

The set of operations is then repeated over a time window shifted in time.

The invention claimed is:

1. A method for detecting a substantially invariant rotation axis of a motion of a mobile body equipped with one of an inertial or magnetic sensor with three sensitive axes, the method comprising the following steps:
    acquiring physical measurements with respect to the three sensitive axes by the inertial or magnetic sensor, the physical measurements comprising at least three samples at different times during motion of the mobile body;
    estimating from the at least three samples a substantially invariant rotation axis in the physical measurements space; and
    identifying the estimated substantially invariant rotation axis as the substantially invariant rotation axis of the motion.

2. The method according to claim 1 further comprising the following steps:
    calculating an indicator of variations of the rotation axis;
    comparing the value of the indicator with a predetermined threshold value; and validating the estimated substantially invariant rotation axis as the substantially invariant rotation axis of the motion if the value of the indicator is less than the predetermined threshold value, which is substantially equal to the value of the noise affecting the physical measurements from the inertial or magnetic sensor.

3. The method according to claim 1, wherein the inertial or magnetic sensor comprises one of an accelerometer with three sensitive axes, a magnetometer with three sensitive axes, or a rate gyro with three sensitive axes.

4. The method according to claim 3, wherein the estimated substantially invariant rotation axis corresponds to the axis for which the standard deviation of the values of the physical measurements projected onto the axis is minimized for a magnetometer or an accelerometer, and maximized for a rate gyro.

5. The method according to claim 4, wherein estimating a substantially invariant rotation axis comprises a step of calculating by analysis into principal components, the third principal component corresponding to the coordinates of the substantially invariant rotation axis in the physical measurements space.

6. The method according to claim 4, wherein estimating a substantially invariant rotation axis comprises a step of calculating least squares applied to a linear combination of the physical measurements.

7. The method according to claim 4, further comprising, if the standard deviation is substantially equal to the standard deviation of noise affecting the inertial or magnetic sensor, the estimated rotation axis is validated as the substantially invariant rotation axis of the motion.

8. The method according to claim 1, wherein the inertial or magnetic sensor comprises a magnetometer or an accelerometer and estimating a substantially invariant rotation axis comprises a step of vectorial calculation on the physical measurements.

9. A method for estimating a motion of a mobile body equipped with one of an inertial or magnetic sensor with three sensitive axes, the motion comprising rotation about a substantially invariant axis, the method comprising the following steps:
    detecting a substantially invariant rotation axis by the detection method according to claim 1; and
    determining a rotation angle of the mobile body about the substantially invariant rotation axis.

10. The method according to claim 9, wherein the inertial or magnetic sensor comprises a magnetometer or a goniometer and the mobile body is also equipped with an accelerometer, and wherein the method further comprises a step of determining the acceleration of the mobile body.

11. A method for calibrating an inertial or magnetic sensor with three sensitive axes for determining a rotation matrix suitable for transforming coordinates expressed in a measurement frame of reference of the sensor into coordinates expressed in a predetermined frame of reference stationary with respect to a mobile body carrying the sensor, the method comprising the following steps:
    acquiring at least two series of physical measurements by the sensor respectively corresponding to the rotation of the mobile body with respect to at least two of the three axes of the predetermined frame of reference;
    determining from each of the two series of coordinates of each of the rotation axes corresponding to one of the at least two axes of the predetermined frame of reference in the frame of reference of the physical measurements from the sensor according to the detection method of claim 1; and
    generating a rotation matrix from the determined coordinates of the at least two rotation axes.

12. The method according to claim 11, wherein the sensor is integrated into a casing, and wherein axes of the predetermined frame of reference are defined by edges of the casing.

13. The method according to claim 11, wherein the sensor is positioned on an anatomical feature, and wherein the predetermined frame of reference corresponds to an anatomical frame of reference defined by three anatomical rotation axes of the anatomical feature.

14. A method for detecting a substantially invariant rotation axis of a motion of a mobile body equipped with one of an inertial or magnetic sensor with three sensitive axes, the method comprising the following steps:
    acquiring physical measurements with respect to the three sensitive axes by the inertial or magnetic sensor, the physical measurements comprising at least three samples at different times during motion of the mobile body:
    estimation from the at least three samples a substantially invariant rotation axis in the physical measurement space; and
    identifying the estimated substantially invariant rotation axis as the substantially invariant rotation axis of the motion; and
    transforming coordinates of the estimated substantially invariant rotation axis in a measurement frame of reference of the inertial or magnetic sensor into coordinates in a geophysical frame of reference.

15. A method for detecting a substantially invariant rotation axis of a motion of a mobile body, wherein the mobile body is equipped with a magnetometer having three sensitive axes and an accelerometer having three sensitive axes, the method comprising the following steps:
    acquiring physical measurements with respect to the three sensitive axes by the magnetometer and the accelerometer, respectively, the physical measurements comprising at least three samples at different times during motion of the mobile body;
    estimating from the at least three samples a substantially invariant rotation axes in the physical measurements spaces of said magnetometer and said accelerometer, respectively; and
    validating the substantially invariant rotation axis of the motion of a linear combination of the estimated rotation axes for said physical measurements from the magnetometer and from the accelerometer, wherein coefficients of the combination are not limited between 0 and 1, their sum being equal to 1, and wherein the coefficients are a function of the values of the indicators of the variations of the rotation axes of the magnetometer or the accelerometer, or both.

16. A device for detecting a substantially invariant rotation axis of a motion of a mobile body equipped with one of an inertial or magnetic sensor with three sensitive axes, wherein the device comprises:
    a sensor acquiring physical measurements with respect to the three sensitive axes of the inertial or magnetic sensor, the physical measurements comprising at least three samples at different times during motion of the mobile body;
    means for estimating from the at least three samples a substantially invariant rotation axis in the physical measurements space; and
    means for identifying the estimated substantially invariant rotation axis as the substantially invariant rotation axis of the motion.

* * * * *

UNITED STATES PATENT AND TRADEMARK OFFICE
CERTIFICATE OF CORRECTION

| | | |
|---|---|---|
| PATENT NO. | : 7,890,291 B2 | Page 1 of 1 |
| APPLICATION NO. | : 12/108981 | |
| DATED | : February 15, 2011 | |
| INVENTOR(S) | : Christelle Godin et al. | |

It is certified that error appears in the above-identified patent and that said Letters Patent is hereby corrected as shown below:

In the Claims

In column 16, claim 14, line 18, before "from the at least three" replace "estimation" with --estimating--.

Signed and Sealed this
Fourth Day of October, 2011

David J. Kappos
*Director of the United States Patent and Trademark Office*